United States Patent
Benz et al.

(10) Patent No.: US 8,007,541 B2
(45) Date of Patent: *Aug. 30, 2011

(54) SUCTION STENT

(75) Inventors: Stefan Benz, Freiburg (DE); Frank Pfeffer, Sölden (DE)

(73) Assignee: MNET GmbH Medizinische Datensysteme, Munich (DE)

(*) Notice: Subject to any disclaimer, the term of this patent is extended or adjusted under 35 U.S.C. 154(b) by 0 days.

This patent is subject to a terminal disclaimer.

(21) Appl. No.: 12/661,143

(22) Filed: Mar. 11, 2010

(65) Prior Publication Data

US 2010/0174381 A1 Jul. 8, 2010

Related U.S. Application Data

(63) Continuation of application No. 11/301,576, filed on Dec. 13, 2005, now Pat. No. 7,691,153, which is a continuation of application No. PCT/EP2004/006311, filed on Jun. 11, 2004.

(30) Foreign Application Priority Data

Jun. 13, 2003 (DE) .................................. 103 27 231

(51) Int. Cl.
A61F 2/82 (2006.01)
A61F 2/84 (2006.01)

(52) U.S. Cl. .................. 623/23.7; 623/1.11; 623/1.15
(58) Field of Classification Search ................. 623/1.11, 623/1.12, 1.13, 1.24, 1.27, 23.7
See application file for complete search history.

(56) References Cited

U.S. PATENT DOCUMENTS

| | | | |
|---|---|---|---|
| 5,693,065 A * | 12/1997 | Rains, III | 606/184 |
| 5,785,679 A | 7/1998 | Hogendijk et al. | |
| 2001/0029349 A1 | 10/2001 | Leschinsky | |
| 2002/0016626 A1* | 2/2002 | DiMatteo et al. | 623/1.13 |
| 2002/0091436 A1* | 7/2002 | Phelps et al. | 623/1.11 |

FOREIGN PATENT DOCUMENTS

| | | |
|---|---|---|
| WO | WO 01/21108 | 3/2001 |
| WO | WO 02/098324 | 12/2002 |
| WO | WO 03/030981 | 4/2003 |
| WO | WO 03/090830 | 11/2003 |

* cited by examiner

Primary Examiner — Alvin J Stewart
Assistant Examiner — Yashita Sharma
(74) Attorney, Agent, or Firm — Klauber & Jackson LLC

(57) ABSTRACT

The present invention relates to a stent for introduction into a hollow organ, in particular the gastrointestinal tract, of a human or animal patient, which brings about vacuum sealing of leaks, such as anastomosis insufficiencies, in the hollow organ.

19 Claims, 1 Drawing Sheet

SUCTION STENT

The present application is a continuation of U.S. Ser. No. 11/301,576, filed Dec. 13, 2005 now U.S. Pat. No. 7,691,153 which is a Continuation of co-pending PCT Application No. PCT/EP2004/006311 filed Jun. 11, 2004, which in turn claims priority from German Application Serial No. 103 27 231.3 filed on Jun. 13, 2003. Applicants claim the benefits of 35 U.S.C. §120 as to the PCT application and priority under 35 U.S.C. §119 as to said German application, and the entire disclosures of both applications are incorporated herein by reference in their entireties.

The present invention relates to a stent for introduction into a hollow organ, in particular the gastrointestinal tract, of a human or animal patient, which brings about vacuum sealing of leaks, such as anastomosis insufficiencies, in the hollow organ.

Leaks in surgical sutures (anastomoses) in the gastrointestinal tract are the most dangerous and thus the most significant complication after operations in the abdominal region. In the event of leaks, the contents of the stomach or intestine pass into the abdominal cavity and thus lead to peritonitis which even nowadays is still fatal in about 20% of cases. Treating such a leak is dependent on the exact location and the damage which has already occurred owing to the escaped contents of the intestine. In the best case, healing of the suture is delayed and the functional result of the operation, in other words, for example, continence, is impaired. Frequently, however, considerably more invasive measures such as a reoperation with removal of the intestinal continuity and fitting of a colostomy are required in order not to endanger the patient's life. The process of fitting a colostomy can only be reversed in a fraction of cases.

Attempts have already been made, in cases in which removal of the continuity of the gastrointestinal tract is not possible, to seal anastomosis insufficiencies using an endoscopically placed endoluminal covered stent, in particular made of metal (self-expandable metal stents with a plastics material sheath). These stents were originally developed for treating stenosing tumours in the oesophagus and are commercially available, for example, from Boston Scientific and Microvasive (for example Ultraflex, covered).

However, the previously available systems were successful in adequately sealing the suture in hollow organs of this type only in a small proportion of cases, so this procedure could not gain acceptance as a standard.

DE-A-199 49 334 describes, for example, a colon stent intended for implantation in a hollow organ of the human body, in particular the intestine. The stent disclosed in this document comprises, in an otherwise conventional configuration, means for detachably fixing the stent in the interior of the hollow organ, in particular the intestine, in order to prevent spontaneous detachment of the stent in the gastrointestinal tract.

The stents known in the prior art have specific drawbacks in particular when used in the gastrointestinal tract.

The known stents thus do not generally achieve sufficient sealing of the defect, for example a surgical suture. This can generally be attributed to the incongruency of the applied stent with the irregularly shaped intestinal wall. Self-expandable stents with high restoring forces cannot be used to achieve complete sealing in the region of untight sutures either as this could lead to further damage or even bursting of the suture.

If, in exceptional cases, complete sealing of the defect is actually achieved, the contents which have issued from the hollow organ, in particular the contents of the intestine, cannot drain away. Formation of an abscess at the suture therefore virtually inevitably occurs, in particular in the gastrointestinal tract, and there is thus further endangering of the local situation and of the patient.

The object of the present invention is therefore to provide a stent which effectively seals any local defects, e.g. untight surgical sutures, and at the same time effectively removes any accumulations of fluid at such defects, in hollow organs of the human or animal body.

This object is achieved by the stent of the present invention characterised in the claims.

In particular, according to the invention a stent for introduction into a hollow organ of the human or animal body, in particular the gastrointestinal tract, primarily the oesophagus or the intestine, for example rectum, sigma, colon descendens or colon transversum, is provided comprising a radially expandable tubular hollow body open in the longitudinal direction,
 a porous shapeable material radially sheathing the hollow body at least in certain regions and
 a drainage means introduced into the aforementioned porous shapeable material and which is configured to apply a subnormal pressure, e.g. a vacuum, wherein the lumen of the hollow body is air- and water-tight with respect to the porous shapeable material.

The present problem of, as far as possible, completely sealing defects in hollow organs and the simultaneous possibility of removing liquid which has issued from the hollow organ such as, for example, the contents of the intestine, is thus solved according to the invention in that the defect, for example caused by an anastomosis insufficiency, is vacuum sealed.

The radially expandable tubular hollow body, open in the longitudinal direction, of the stent according to the invention can, for example, be a self-expandable metal or plastics material stent, as is described for example in U.S. Pat. No. 5,876,448. The disclosure of this document in this regard is an explicit component of the present disclosure. A stent according to the present invention is an expandable hollow body, wherein expansion is taken to mean any type of increase in volume, in particular by inflation of the hollow body or by mechanical expansion (optionally widening) of the hollow body. A stent of this type is introduced into the body cavities (for example with a tube-like structure) wherein a stent can, for example, also be taken to mean a balloon, this in turn typically being expanded by inflation. The stent is sheathed, at least in certain regions, preferably substantially completely radially, by the porous shapeable material. The porous shapeable material can be a closed-pore material, i.e. in the form of a foam, or an open-pore material, i.e. in the manner of a sponge. Preferred materials for this purpose are plastics material foams, for example those which consist of polyurethanes, polyvinyl alcohols or mixtures of such plastics materials or contain these. At least a portion of the stent according to the invention is thus e.g. a self-expandable metal or plastics material stent with a plastics material sheath. The other portion, if any, is a usually constructed metal or plastics material stent with a plastics material sheath without being self-expandable.

The luminal diameter of the stent according to the invention, i.e. the radially expandable hollow body is, for example, in the range of about 10 to 50 mm, preferably 15 to 35 mm, in particular 15 to 30 mm, most particularly preferably it is about 25 mm (for example in applications in the colon region) or about 18 mm (for example for use in the oesophagus). In any case, the diameter of the stent is selected such that, depending on the area of application, the passage of corresponding material through the respective hollow organ—the passage of food in the case of the intestinal tract—is not obstructed.

According to the invention, the shapeable porous material, for example a foam, is air- and water-tight from the lumen. According to a preferred embodiment, if the hollow body is not primarily tight, it is sealed, at least in certain regions, in particular completely, by an air- and water-tight film. Plastics material films which contain, for example, a polyurethane, latex and/or silicone or consist thereof are particularly advantageous for this purpose.

The film may be in the form of a winding around the hollow body, wherein contact points obviously have to be sealed and this can easily be brought about, for example by a weld in the case of a plastics material film. However, films according to the invention, in particular plastics material films which are tubular are preferred. The film preferably projects beyond the body at least at one end, more preferably it projects beyond the hollow body at both ends. It is also preferred according to the invention if the film, for example a tubular plastics material film, projects beyond the hollow body at both ends and if the diameter further increases toward the periphery.

According to a further preferred embodiment of the present invention, the diameter of the hollow body increases in one or both end region(s). It is preferred if the diameter increases at both end regions. In this case the thickness of the porous shapeable material, for example the foam, decreases in the end region(s) of the hollow body, and it is particularly preferred if its thickness decreases to the same extent as the diameter of the hollow body increases in the end region(s). The porous shapeable material, for example, a plastics material foam, is present, for example, in a thickness of about 5 to about 10 mm.

The stent according to the invention also comprises a drainage means introduced into the porous shapeable material which is configured to apply a subnormal pressure, e.g. a vacuum (suction drainage means). According to a preferred embodiment, the suction drainage means is introduced into the shapeable porous material for example from the lumen through a point of passage in the film according to the invention. It should be ensured here that the point of passage in the film is sealed from the drainage means which is constructed, for example, from a corresponding plastics material tube, as is known to a person skilled in the art. Preferred embodiments of such seals are disclosed, for example, in DE-A-44 33 450 to which the disclosure in this regard refers in its entirety. According to a particular embodiment, the seal at the point of passage is realised by an easily deformable, non-flowing sealant. This sealant is preferably a silicone, a hydrocolloid, a lyogel, in particular a hydrogel, and may be easily manually deformed and optionally adapted to irregularities which exist at the passage in the drainage means tube or possible folding of the film, the sealant penetrating the existing leaks and sealing them. The deformability and the flow properties of the sealant are preferably adjusted such that easy deformability and good penetration into the leaks are ensured but draining away of the sealant under the effect of the pressure gradient applied to the drainage means is prevented.

The entire construction of the stent according to the invention is preferably completely expandable and can be brought to the application site in the organ, in particular the gastrointestinal tract, preferably the oesophagus, intestine, primarily rectum, sigma, colon descendens or colon transversum, by conventional application measures.

The invention will be described hereinafter with reference to the accompanying drawings and with the aid of an exemplary embodiment of the stent according to the invention.

Figure 1:
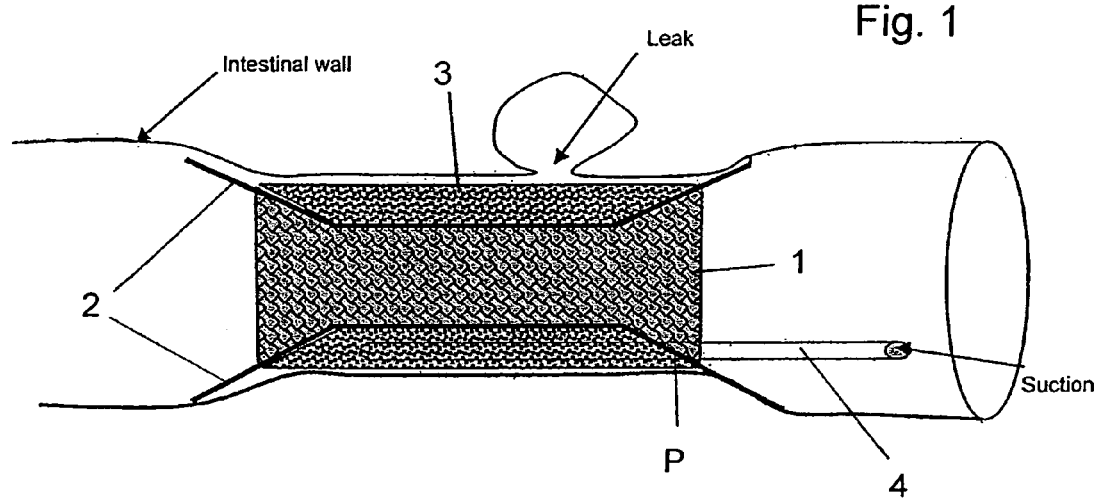
FIG. 1 shows a longitudinal section through a stent applied according to the invention in the intestine, which exhibit an anastomosis insufficiency.
Figure 2:
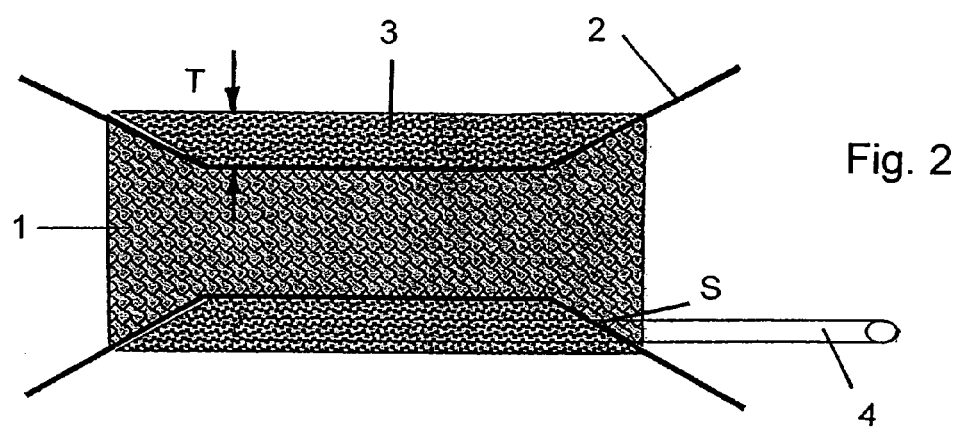
FIG. 2 is a schematic view of a longitudinal section through a stent according to the invention.
Figure 3:
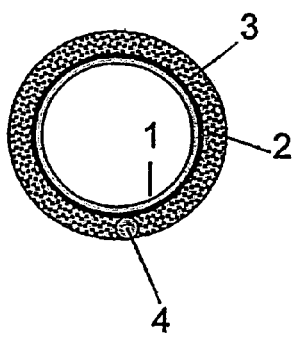
FIG. 3 is a further schematic view of a cross-section through the stent shown in FIG. 2.

Referring to FIGS. 1 to 3, according to the invention an endoscopically placeable self-expandable stent (metal or plastics material) (1) is circularly encased by a soft plastics material foam (3). The foam is sealed from the lumen by an air- and water-tight plastics material film (2). A suction drainage means (4) is introduced into the foam (3) via this plastics material film (2) from the lumen, the film (2) being sealed from the drainage means (4) at the point of passage. The diameter of the stent (1) increases toward both ends while the thickness of the foam (3) decreases. The sealing film (2) circularly projects beyond the stent (1), the diameter further increasing toward the periphery. The entire construction is conventionally expandable and is brought to the application site via a wire-guided applicator with endoscopic or X-ray control; in this case it is introduced into the intestine, which exhibits a leak, for example an anastomosis insufficiency, at the application site. As shown in FIG. 1, the stent is preferably placed via an endoscopically positioned guide wire in such a way that the leak comes to rest in the centre of the stent. After releasing the stent (self-expansion) the stent expands to its predetermined size and then loosely rests on the intestinal wall, as FIG. 1 shows. The suction drainage means (4) provided on the stent is led out peranally, perorally or pernasally, depending on the area of application of the stent, and a suction is applied. The intestinal wall is circularly sucked onto the stent as a result, so the stent completely covers the leak, and egress of fluid from the hollow organ, in the present case the intestine, is prevented. At the same time, any existing fluid, which has accumulated in the region of the leak outside the intestinal wall, is sucked up and away by the suction drainage means. The stent can accordingly remain in situ until the patient's condition has stabilised. The stent can then be extracted.

Therefore, in a further aspect of the present invention a method for sealing leaks present in a hollow organ of the human or animal body, in particular in the gastrointestinal tract, for example the above-mentioned parts of the intestine, is provided, which comprises the following steps:

(a) introducing the stent according to the invention into the hollow organ so the leak of the hollow organ is located at the longitudinal side of the stent, preferably in the region of the centre of the longitudinal side, in particular exactly in the centre, (b) releasing the stent, so it expands to its predetermined size and (c) applying a subnormal pressure, e.g. a vacuum (suction) to the drainage means of the stent.

An intraluminal stent as the carrier for a vacuum seal for leaks in hollow organs and a corresponding method for sealing the leaks are thus provided, according to the invention, for the first time. Using this method it is in particular possible to reliably seal an anastomosis insufficiency, in particular in the region of the colon and rectum, by an intraluminal intervention. The stent according to the invention therefore assists management of patients with critical anastomosis conditions, in a particularly positive manner. The use of the stent according to the invention leads to survival of the patient in an otherwise life-threatening condition. When using the stent according to the invention the patient will be confined to about 5 days' to 1 week's bed rest (to ensure a reliable seal).

Without the present invention an operation would generally be required in situations of this type, and—in the case of anastomosis insufficiencies in the region of the intestine—fitting of a colostomy would frequently be required, and this cannot be reversed in all cases and sometimes can only be reversed with considerable morbidity.

The invention claimed is:

1. A stent for introduction into a hollow organ of the human or animal body comprising: a radially expandable tubular hollow body (1) having a lumen and a diameter that increases at one or both end region(s) of the hollow body, a porous shapeable material (3) radially sheathing the hollow body (1) at least in certain regions, wherein the thickness (T) of the material (3) decreases at the end region(s) of the hollow body as the diameter of the hollow body (1) increases in the end region(s), and a drainage means (4), wherein the drainage means is introduced into the porous shapeable material (3) and configured to apply suction or a sub-normal pressure or a vacuum, wherein the lumen of the hollow body (1) is air- and water-tight with respect to the material (3).

2. A stent according to claim 1, wherein the material (3) substantially completely radially sheaths the hollow body (1).

3. A stent according to claim 1, wherein the porous shapeable material (3) is tubular and has substantially the same longitudinal extent as the hollow body (1).

4. A stent according to claim 1, wherein the material (3) is air- and water-tight, at least in certain regions.

5. A stent according to claim 1, wherein the material (3) comprises a closed-pore material, in the form of a foam, which is air- and water-tight.

6. A stent according to claim 1, wherein the drainage means (4) is introduced into the material (3) via a point of passage (P) in an air- and water-tight layer.

7. A stent according to claim 6, wherein, at the point of passage (P), the hollow body (1) is sealed from the drainage means (4) by an easily deformable, non-flowing sealant (S).

8. A stent according to claim 7, wherein the sealant (S) comprises a material selected from the group consisting of a silicone, hydrocolloid or lyogel, such as a hydrogel.

9. A stent according to claim 1, wherein the material (3) is a plastics material foam.

10. A stent according to claim 9, wherein the plastics material foam is selected from the group consisting of polyurethanes and polyvinyl alcohols.

11. A stent according to claim 1, wherein the hollow body (1) is sealed from the material (3) by an air- and water-tight layer (2).

12. A stent according to claim 11, wherein the layer (2) is tubular.

13. A stent according to claim 11, wherein the layer (2) contains a plastics material or consists thereof.

14. A stent according to claim 13, wherein the plastics material is selected from the group consisting of polyurethanes, latex and silicone.

15. A stent for introduction into a hollow organ of the human or animal body comprising: a radially expandable tubular hollow body having a lumen and a diameter that increases at one or both end region(s) which, when expanded, is open in the longitudinal direction, a porous shapeable material (3) which radially sheaths the hollow body at least in certain regions wherein the thickness (T) of the material (3) decreases at the end region(s) of the hollow body as the diameter of the hollow body (1) increases in the end region(s), and a drainage means, wherein the drainage means is introduced into the material and which is configured to apply a sub-normal pressure or vacuum in the material, wherein the lumen of the hollow body is sealed so as to be air- and water-tight with respect to the material.

16. A method of using a stent for sealing a leak in a hollow organ of the human or animal body, the stent comprising: a radially expandable tubular hollow body having a lumen and a diameter that increases at one or both end region(s); a porous shapeable material which radially sheaths the hollow body at least in certain regions wherein the thickness (T) of the material (3) decreases at the end region(s) of the hollow body as the diameter of the hollow body (1) increases in the end region(s); and a drainage means, wherein the drainage means is introduced into the porous shapeable material and configured to apply a sub-normal pressure or a suction; the method comprising the steps:
(a) introducing the stent into the hollow organ so the leak of the hollow organ is located at the longitudinal side of the stent, (b) expanding the stent to its predetermined size, and (c) applying a subnormal pressure or a suction to the drainage means of the stent.

17. A method according to claim 16, wherein the step of introducing the stent into the hollow organ comprises introducing the stent into the hollow organ so that the leak of the hollow organ is located in the region of the centre of the longitudinal side of the stent.

18. A method according to claim 16, wherein the step of expanding the stent comprises expanding the hollow body to its predetermined size.

19. A method according to claim 16, wherein the step of expanding the stent comprises releasing the stent so it expands to its predetermined size.

* * * * *